US012595455B2

(12) United States Patent
Lee

(10) Patent No.: US 12,595,455 B2
(45) Date of Patent: Apr. 7, 2026

(54) SCREEN CHANGING DEVICE, AND SYSTEM AND METHOD OF REDUCING THE SIZE OF LIVING TISSUE IN USING THE SAME

(71) Applicant: Jun Seok Lee, Busan (KR)

(72) Inventor: Jun Seok Lee, Busan (KR)

( * ) Notice: Subject to any disclaimer, the term of this patent is extended or adjusted under 35 U.S.C. 154(b) by 646 days.

(21) Appl. No.: 18/013,283

(22) PCT Filed: Oct. 21, 2022

(86) PCT No.: PCT/KR2022/016190
§ 371 (c)(1),
(2) Date: Dec. 28, 2022

(87) PCT Pub. No.: WO2023/068883
PCT Pub. Date: Apr. 27, 2023

(65) Prior Publication Data
US 2024/0034980 A1      Feb. 1, 2024

(30) Foreign Application Priority Data

Oct. 22, 2021      (KR) ......................... 10-2021-0141624
Oct. 19, 2022      (KR) ......................... 10-2022-0134712

(51) Int. Cl.
*C12M 1/26*          (2006.01)
*C12M 1/00*          (2006.01)
(52) U.S. Cl.
CPC ............ *C12M 33/04* (2013.01); *C12M 23/50* (2013.01); *C12M 33/12* (2013.01); *C12M 33/14* (2013.01)

(58) Field of Classification Search
CPC ...... C12M 33/04; C12M 33/12; C12M 33/14; C12M 23/50
USPC ....................................................... 435/283.1
See application file for complete search history.

(56) References Cited

FOREIGN PATENT DOCUMENTS

| | | | | |
|---|---|---|---|---|
| JP | 2007111653 A | * | 5/2007 | |
| JP | 2009183149 A | * | 8/2009 | ............ C12M 47/04 |
| KR | 20200119695 A | | 10/2020 | |
| WO | WO-2020209609 A2 | * | 10/2020 | .............. A61M 1/02 |

OTHER PUBLICATIONS

JP-2009183149-A Machine English Translation (Year: 2009).*
WO2020209609A2 Machine English Translation (Year: 202).*
JP2007111653A (Year: 2007).*

* cited by examiner

*Primary Examiner* — Michael L Hobbs
*Assistant Examiner* — Lenora A Abel
(74) *Attorney, Agent, or Firm* — Bayramoglu Law Offices LLC

(57) ABSTRACT

A screen changing device is proposed. The screen changing device includes a first housing and a second housing configured to be rotated with respect to the first housing. The screen changing device can transit from a first configuration in which a first screen is aligned with a first connector and a second connector to a second configuration in which the first screen is not aligned with the first connector and the second connector and a second screen is aligned with the first connector and the second connector.

14 Claims, 23 Drawing Sheets

SCREEN CHANGING DEVICE, AND SYSTEM AND METHOD OF REDUCING THE SIZE OF LIVING TISSUE IN USING THE SAME

CROSS REFERENCE TO THE RELATED APPLICATIONS

This application is the national phase entry of International Application No. PCT/KR2022/016190 filed on Oct. 21, 2022, which is based upon and claims priority to Korean Patent Applications No. 10-2021-0141624 filed on Oct. 22, 2021 and No. 10-2022-0134712 filed on Oct. 19, 2022, the entire contents of which are incorporated herein by reference.

TECHNICAL FIELD

The present disclosure relates to a screen changing device, and a system and method of reducing the size of a living tissue using the screen changing device. In more detail, the present disclosure relates to a screen changing device that changes any one screen, which reduces the size of a living tissue, to another screen to separate substance that can be used for regeneration treatment and cosmetic treatment from a living tissue, and a system and method of reducing the size of a living tissue using the screen changing device.

BACKGROUND

Living tissues contain various tissues, cells, and substances that can be used for regeneration treatment and cosmetic treatment, so various methods are used to separate the tissues, cells, and substances. In particular, a method of decomposing and centrifugally separating a fat tissue generally using an enzyme is widely used for fat tissues, but there is no appropriate medical enzyme and enzymes that are used have toxicity, so there is controversy over the safety of substances obtained from decomposed fat tissues. Accordingly, there were various attempts to obtain a substance, which can be used for regeneration treatment and cosmetic treatment from fat tissues without using an enzyme. For example, a screen changing device has been disclosed in Korean Patent Application Publication No. 10-2020-0119695. The background described above was kept or obtained by the inventor(s) in the process of deriving the invention and should not be considered as a well-known technology published before the filing of the present disclosure.

SUMMARY

An objective of the present disclosure is to provide a screen changing device that has a plurality of screens having through-holes, which reduce the size of a living tissue and have different sizes, and that can change any one screen in a channel to another screen without separating a container for pressing a living tissue and a container for keeping a living tissue.

Another objective of the present disclosure is to provide a system and method of reducing the size of a living tissue using the screen changing device.

According to an embodiment, a screen changing device includes: a first housing including a first base, an outer wall connected to the base, an inner wall connected to the first base and being opposite to the outer wall, a first space defined between the outer wall and the inner wall, a second space defined by the inner wall, a first connector disposed on the outer wall, and a second connector disposed on the inner wall and in the second space; a second housing including a second base, a supporting wall connected to the second base and disposed in the first space, and a plurality of recesses arranged in a circumferential direction of the supporting wall; and a plurality of screens disposed in the plurality of recesses, respectively, and configured to reduce a size of a living tissue, in which the second housing is configured to be rotated with respect to the first housing from a first configuration in which a first screen of the plurality of screens is aligned with the first connector and the second connector to a second configuration in which the first screen is not aligned with the first connector and the second connector and a second screen of the plurality of screens is aligned with the first connector and the second connector.

In an embodiment, the screen changing device may further include a plurality of caps configured to retain the first screen, which corresponds to a first recess of the plurality of recesses, of the plurality of screens in the first recess.

In an embodiment, the screen changing device may further include a first sealing disposed between the plurality of caps and the outer wall.

In an embodiment, the screen changing device may further include a second sealing disposed between the supporting wall and the plurality of caps.

In an embodiment, the screen changing device may further include a third sealing disposed between the supporting wall and the inner wall.

In an embodiment, the first connector may include: a first protrusion protruding from the outer wall away from the rotation axis; and a first passage defined in the first protrusion.

In an embodiment, the second connector may include: a second protrusion protruding from the inner wall; and a second passage defined in the second protrusion, and the second protrusion may include: a first extension extending from the inner wall toward the rotation axis; and a second extension extending from the first extension in an axial direction of the rotation axis.

In an embodiment, the screen changing device may further include: a guide groove disposed in the first housing; a ball disposed in the second housing; and an elastic member disposed between the guide groove and the ball, in which the ball and the elastic member may be configured to determine a position of the second housing with respect to the first housing.

In an embodiment, the first housing may further include: a third connector disposed on the outer wall; and a fourth connector disposed on the inner wall and in the second space.

In an embodiment, the screen changing device may further include a channel adapter configured to be coupled to the second connector.

In an embodiment, the screen changing device may further include an indicator showing a rotation direction of the second housing.

In an embodiment, the screen changing device may further include a body cap disposed between the inner wall and the second base.

In an embodiment, the first screen may include a first through-hole having a first shape and the second screen may include a second through-hole having a second shape different from the first shape.

According to an embodiment, a system for reducing a size of a living tissue includes: a first syringe; a second syringe; and a screen changing device, in which the screen changing device includes: a first housing including a first base, an outer wall connected to the base, an inner wall connected to the first base and being opposite to the outer wall, a first space defined between the outer wall and the inner wall, a second space defined by the inner wall, a first connector disposed on the outer wall and configured to be connected with the first syringe, and a second connector disposed on the inner wall and in the second space and configured to be connected with the second syringe; a second housing including a second base, a supporting wall connected to the second base and disposed in the first space, and a plurality of recesses arranged in a circumferential direction of the supporting wall; a plurality of screens disposed in the plurality of recesses, respectively, and configured to reduce a size of a living tissue; and a plurality of caps configured to retain the first screen, which corresponds to a first recess of the plurality of recesses, of the plurality of screens in the first recess, in which the second housing is configured to be rotated with respect to the first housing from a first configuration in which a first screen of the plurality of screens is aligned with the first connector and the second connector to a second configuration in which the first screen is not aligned with the first connector and the second connector and a second screen of the plurality of screens is aligned with the first connector and the second connector.

According to an embodiment of the present disclosure, a method of reducing a size of a living tissue using a screen changing device includes: a step of connecting a first syringe and a second syringe as a step of connecting the first syringe and the second syringe to the first connector and the second connector, respectively, in which at least one syringe of the first syringe and the second syringe is empty or includes a living tissue; a step of aligning a first screen of a plurality of screens with the first connector and the second connector; a step of alternately pressurizing the first syringe and the second syringe; a step of aligning a second screen of a plurality of screens with the first connector and the second connector; and a step of alternately pressurizing the first syringe and the second syringe.

According to an embodiment, any one screen position in a channel can be changed to another one screen without separating a container (ex. a syringe) pressurizing a living tissue and a container (ex. a syringe) accommodating a living tissue in a screen changing device including a plurality of screens for reducing the size of a living tissue.

In detail, effects of the present disclosure are as follows.

First, it is possible to change a screen by only rotating a housing.

In the device of the present disclosure in which a plurality of screens having different sizes or shapes of through-holes for making a living tissue fine, when changing a currently selected screen to another screen, it is possible to change a screen corresponding to a container (ex. a syringe), which pressurizes or accommodates a living tissue, to another screen by rotating a second housing with respect to a first housing without separating or replacing the container.

Second, since two sets of connectors making a pair are provided, when a channel through which a living tissue passes is clogged, it is possible to immediately perform a process of reducing the size of a living tissue by connecting a syringe to another set of connectors.

Two syringes that are connected to the screen changing device make a set in a pair, and when a living tissue is pressurized in one syringe, the living tissue of which the size is reduced due to scratching or tearing through a screen is accommodated in another syringe. Accordingly, two connectors that are connected to a syringe also make a set in a pair. In the present disclosure, other spare connectors making a pair are provided so that another connector can be used when a channel through which a living tissue passes is clogged or damaged and cannot be used. That is, two sets of connectors making a pair are provided.

Third, since the direction of rotation for changing a screen is shown, it is possible easily to change a screen to a screen having relatively small through-holes in the process of making a living tissue fine.

When a process of reducing the size of a living tissue using any one screen is finished, the screen should be changed to another screen having small through-holes, and in the present disclosure, an arrow is on the top surface of a first housing, so it is possible to easily change the screen to the screen having small through-holes by rotating the second housing in the direction of the arrow. That is, the arrow provides a guide making it possible to easily select a next screen in the process of reducing the size of a living tissue.

Fourth, when the second housing is rotated to change a screen, it is possible to easily determine the right position of the second housing with respect to the first housing.

Elastic members 172 and balls 173 are disposed in the second housing and guide grooves 112C corresponding to the elastic members and the balls are formed on the first housing, so the positions where the balls are fixed by the guide grooves are positions at which connectors of the first housing corresponds to screens of the second housing. That is, when the second housing is rotated to change a screen, a ball elastically supported by an elastic member is moved (positioned) in another groove at a next position (about 90 degrees), whereby a connector of the housing is accurately positioned at a position corresponding to a screen of the second housing.

Fifth, since through-hole of screens through which a living tissue passes are formed in special shapes, the process of making a tissue fine through scratching or tearing is smoothly performed.

Sixth, it is possible to reduce the size of a living tissue into a desired size by simply and conveniently change a screen.

The process of reducing the size of a living tissue using the device of the present disclosure is described.

i) A set of connectors is aligned with a screen having largest through-holes, an empty container (ex. a syringe) is fastened to one connector and a container having a living tissue therein is fastened to the other connector.

ii) The container having the living tissue therein is pressurized so that the living tissue moves into the empty container through the screen. The process of pressurizing a containers is repeated several times. The living tissue is reduced in size while reciprocating through the through-holes of screen by this repeated pressurization. When the process of reducing the size of a living tissue using a corresponding screen is finished, the screen is changed to a next screen having small through-holes.

iii) According to the changing method, the second housing is rotated with a container coupled in the direction of an arrow on the first housing and the direction of an arrow on the second housing, whereby the container is positioned at a next screen. In this case, a right position is determined by a ball and a guide groove, and when a "click" (a sound by a ball hitting against the surface of a guide groove) is generated, it means that the container is positioned at a right position corresponding to the next screen. In this state, pressurizing a containers is repeated several times. When the process of reducing the size of a living tissue using a corresponding screen is finished, the screen is changed to a next screen having smaller through-holes.

iv) Finally, when the process of reducing the living tissue is finished, the container having the tissue therein is separated from the connector and the tissue in the container is moved to another place.

It is possible to reduce the size of a living tissue into a desired size by conveniently changing screens through the simple operation described above.

Objectives of the screen changing device of the present disclosure are not limited to those described above and other objectives not state herein can be clearly understood by those skilled in the art from the following description.

BRIEF DESCRIPTION OF THE DRAWINGS

Above-mentioned and other aspects, features, and advantages of specific embodiments of the present disclosure will be made apparent from the following detailed description.

REFERENCE NUMERALS

Figure 1:
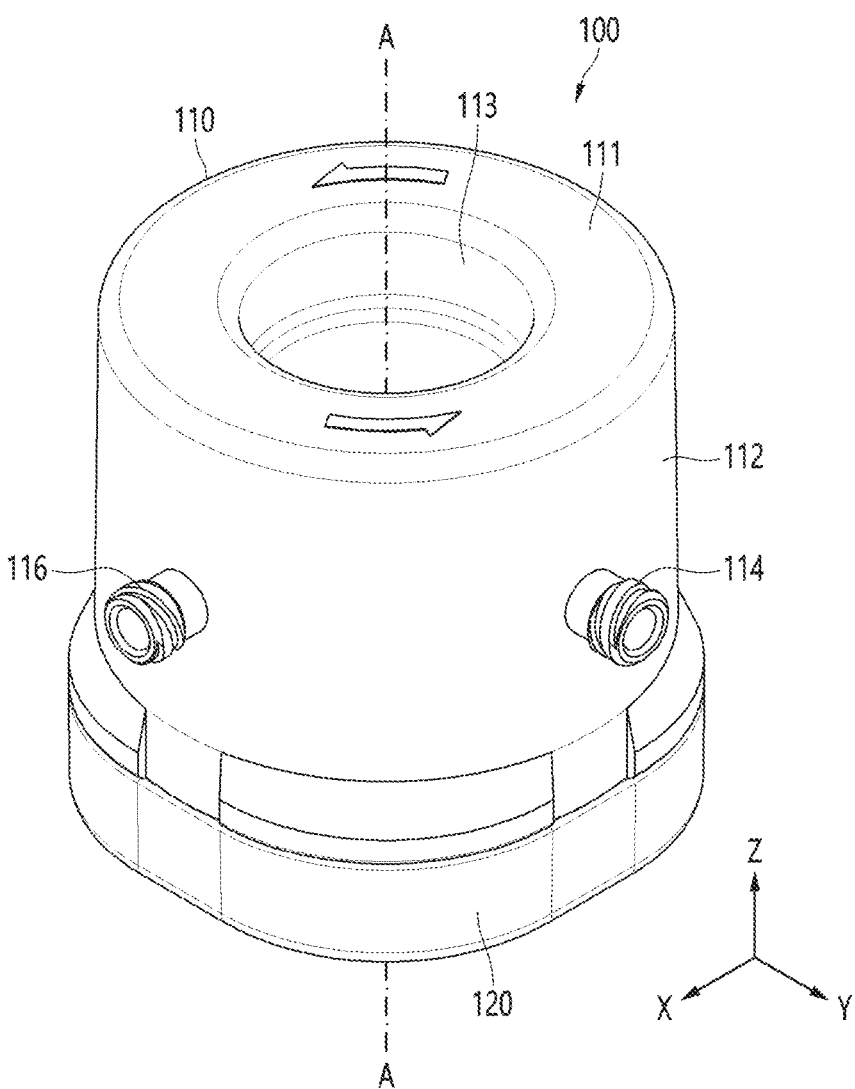
FIG. 1 is a perspective view of a screen changing device according to an embodiment.
Figure 2:
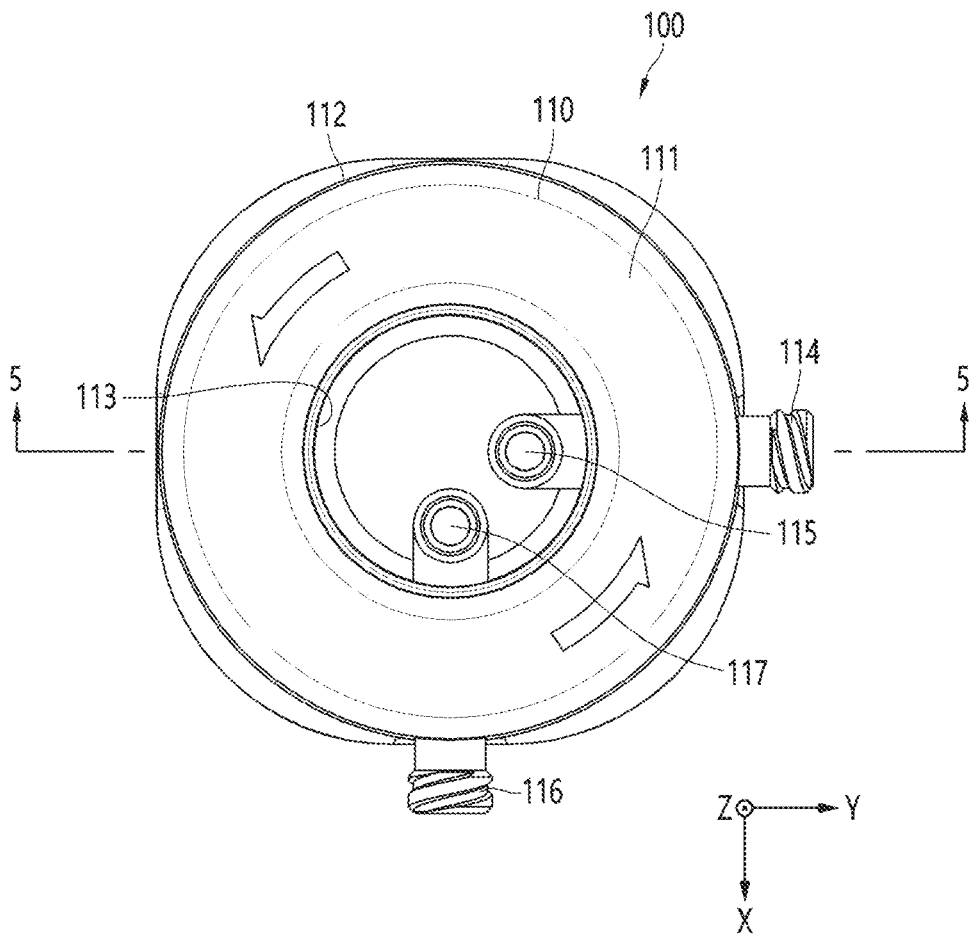
FIG. 2 is a plan view of the screen changing device according to an embodiment.
Figure 3:
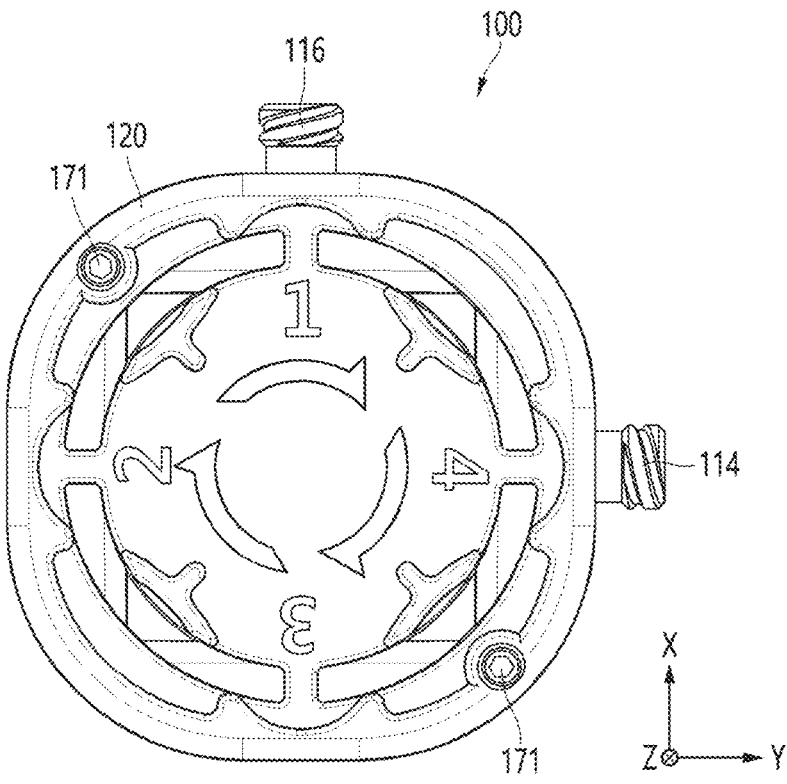
FIG. 3 is a bottom view of the screen changing device according to an embodiment.
Figure 4:
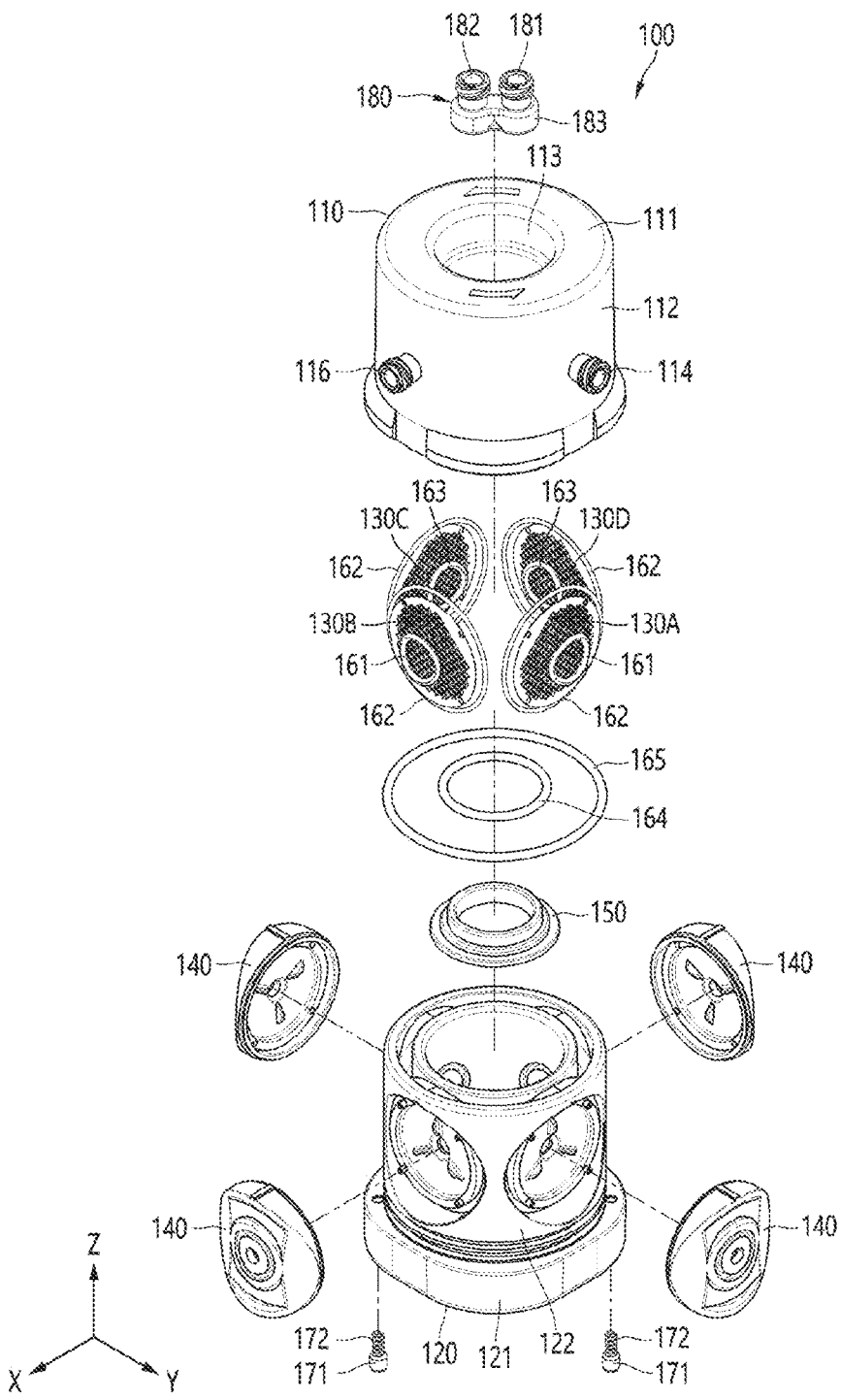
FIG. 4 is an exploded perspective view of the screen changing device according to an embodiment.
Figure 5:
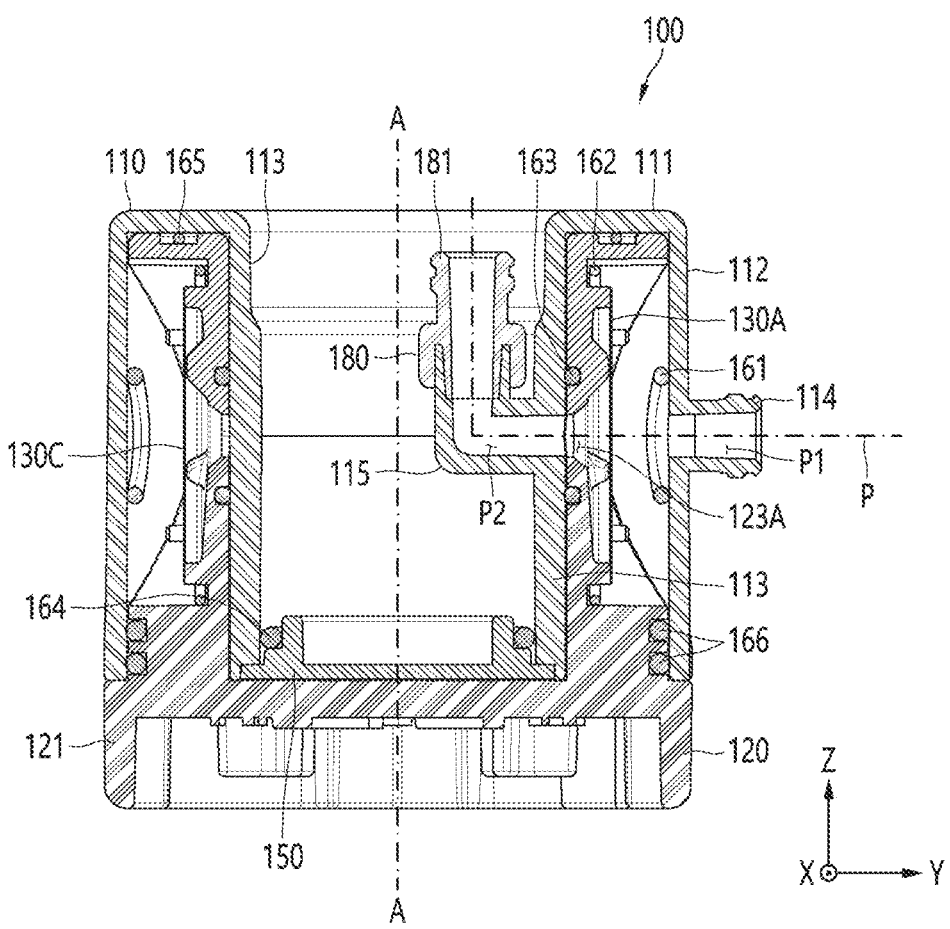
FIG. 5 is a cross-sectional view of the screen changing device of FIG. 2 according to an embodiment taken along line 5-5.
Figure 6:
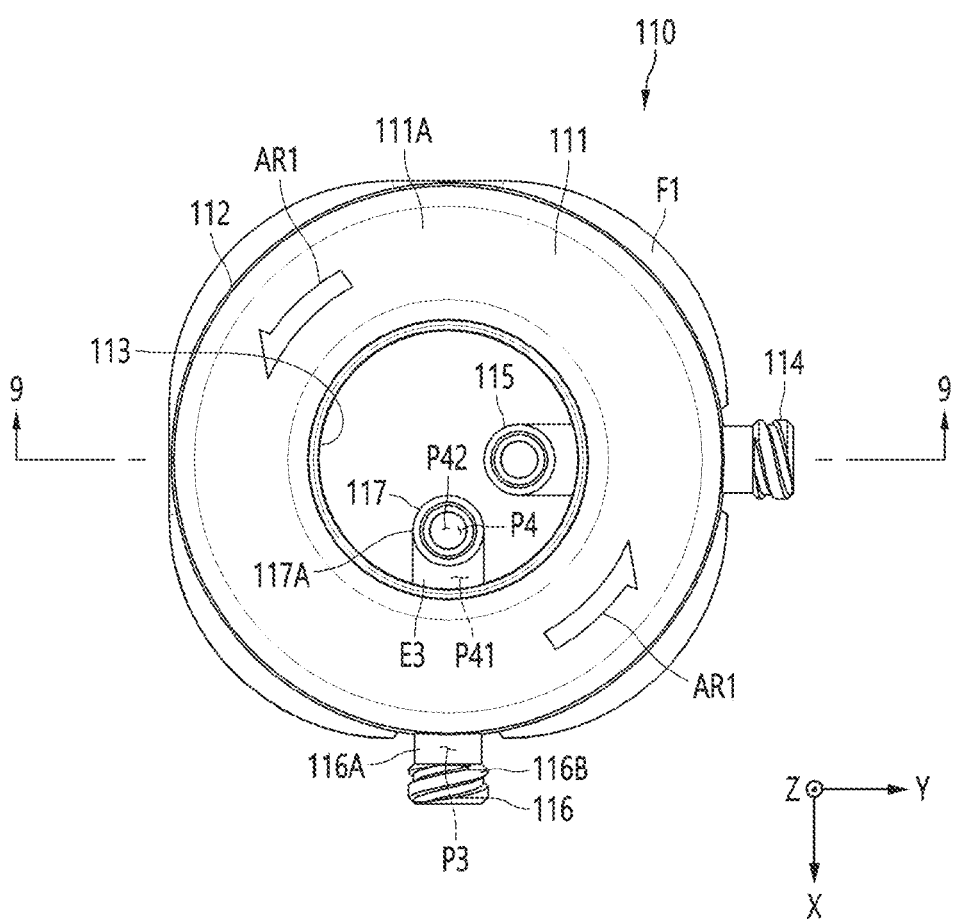
FIG. 6 is a plan view of a first housing according to an embodiment.
Figure 7:
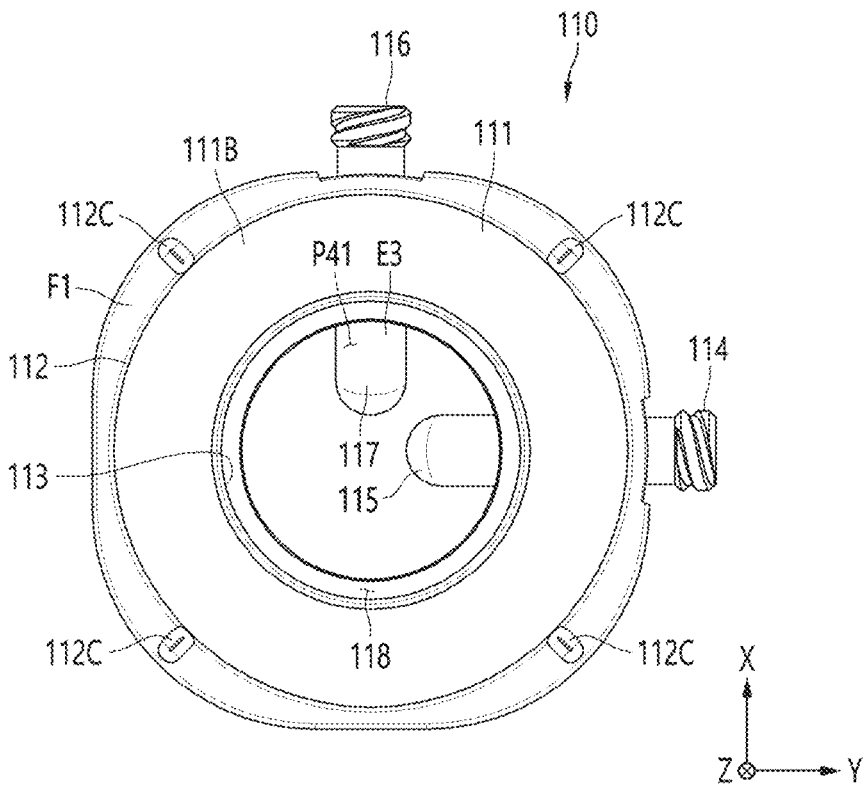
FIG. 7 is a bottom view of the first housing according to an embodiment.
Figure 8:
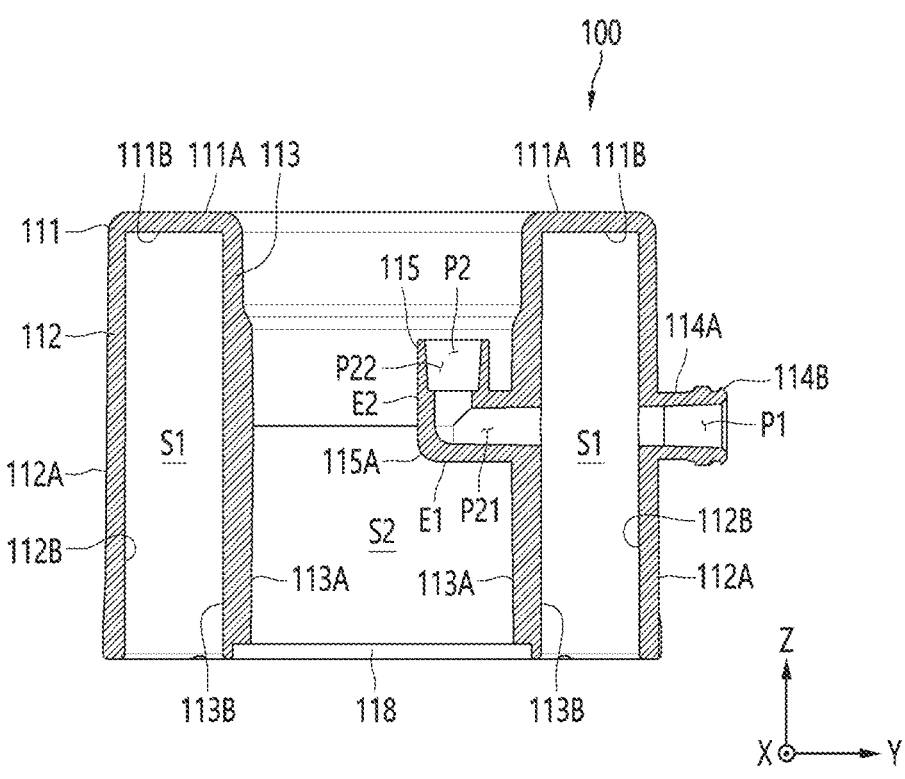
FIG. 8 is a cross-sectional view taken along line 8-8 of the first housing of FIG. 6 according to an embodiment.
Figure 9:
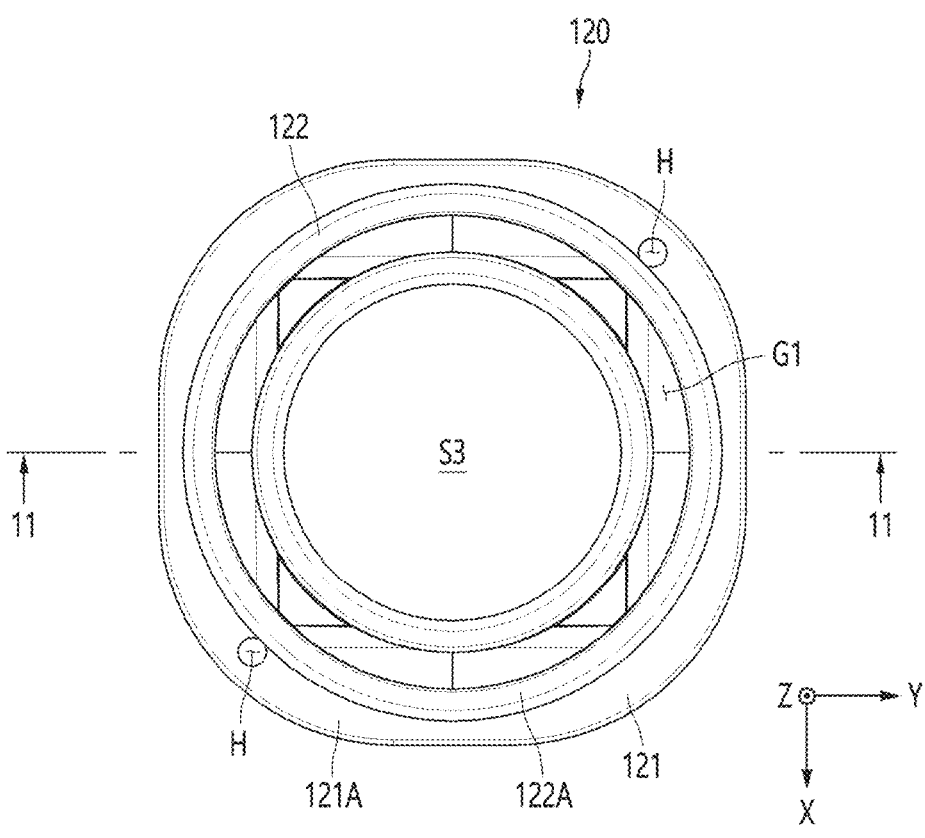
FIG. 9 is a plan view of a second housing according to an embodiment.
Figure 10:
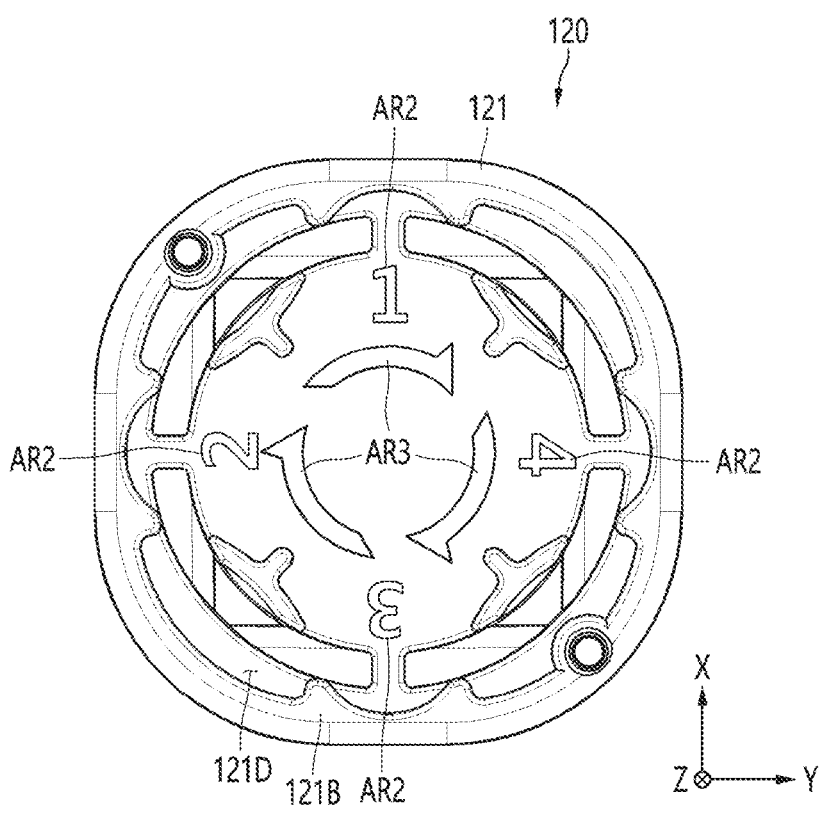
FIG. 10 is a bottom view of the second housing according to an embodiment.
Figure 11:
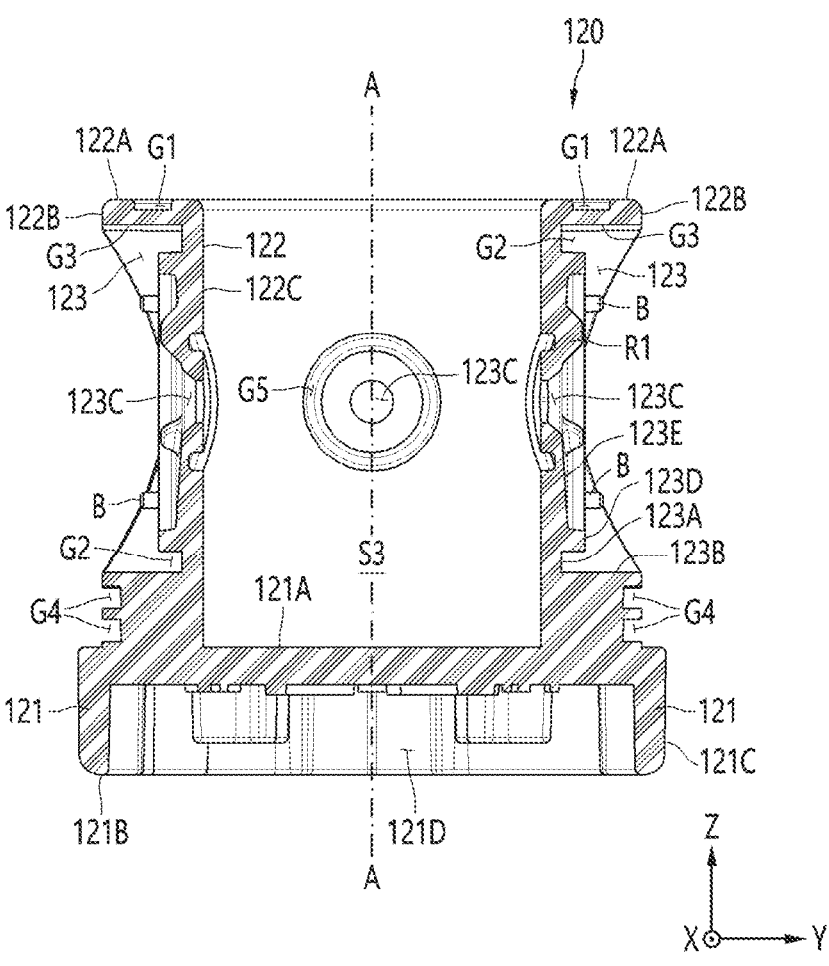
FIG. 11 is a cross-sectional view of the second housing taken along line 11-11 of FIG. 9 according to an embodiment.
Figure 12:
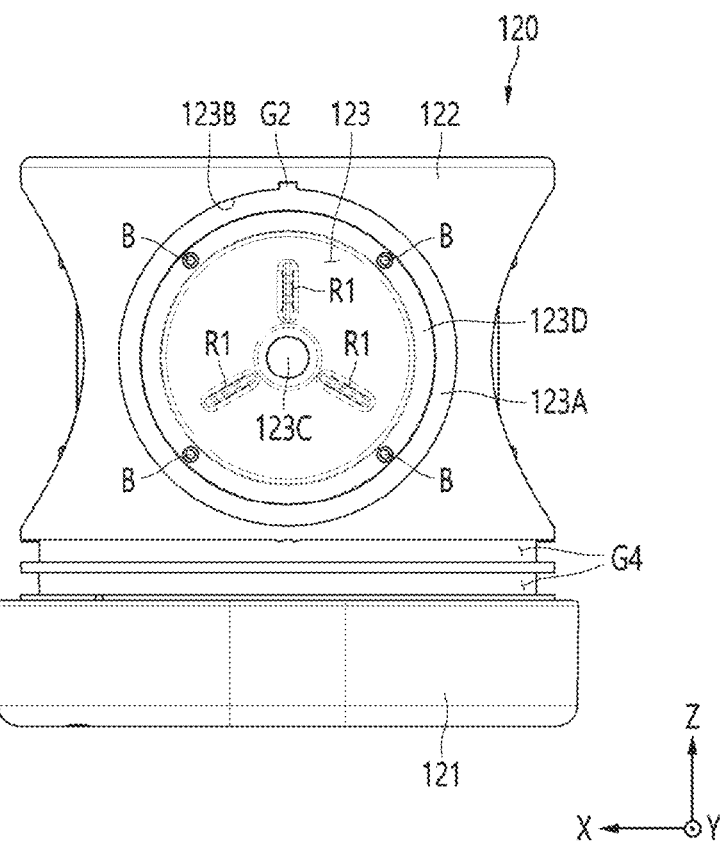
FIG. 12 is a side view of the second housing according to an embodiment.
Figure 13:
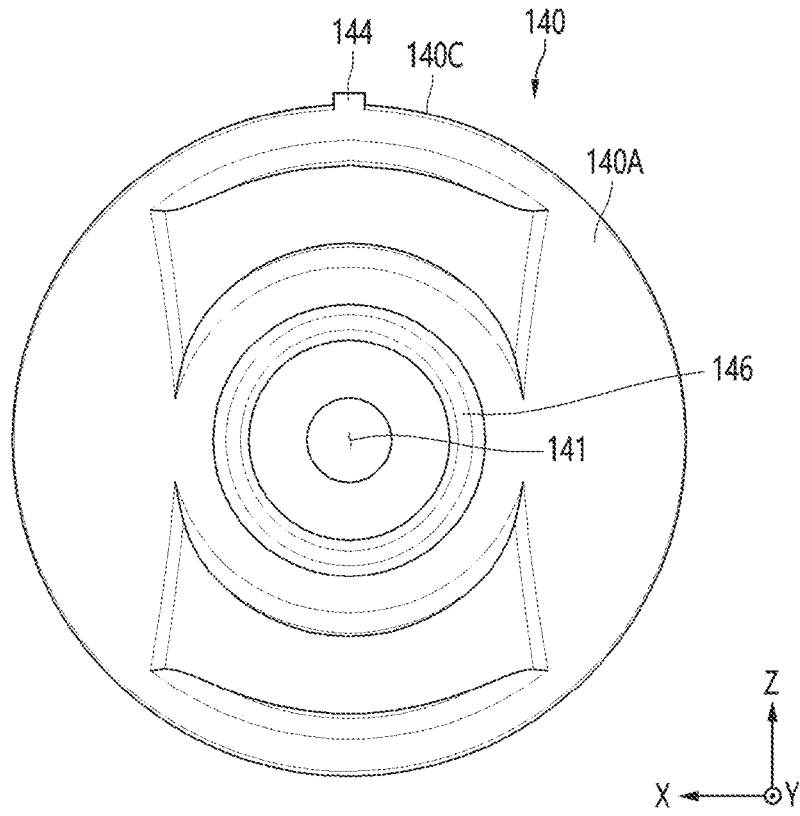
FIG. 13 is a front view of a cap according to an embodiment.
Figure 14:
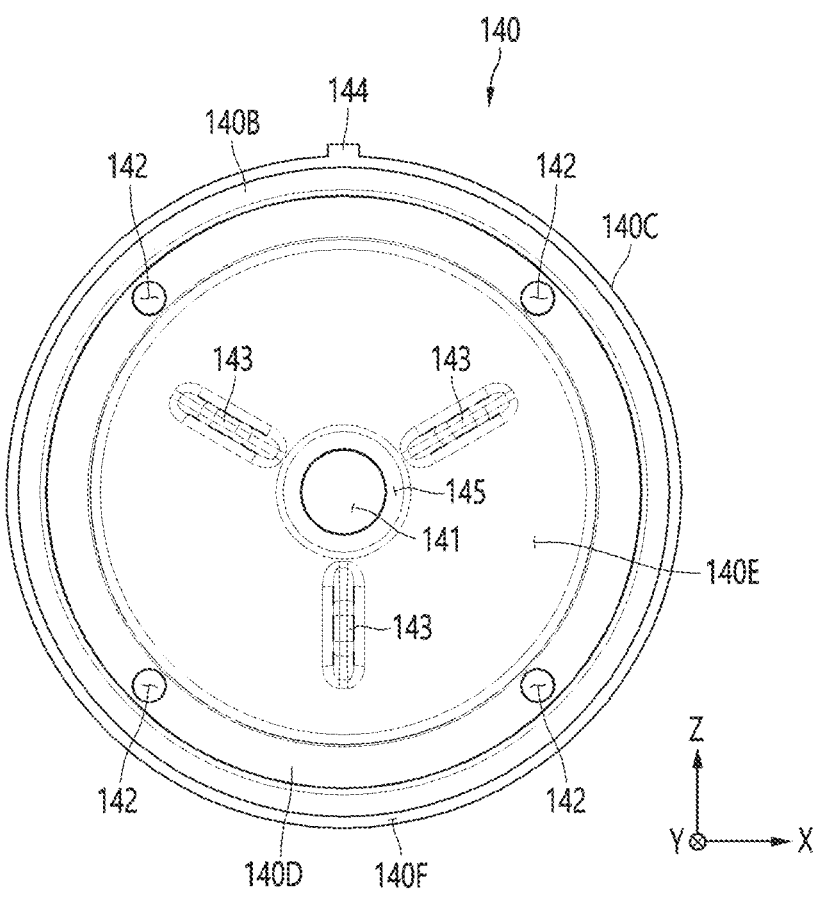
FIG. 14 is a rear view of the cap according to an embodiment.
Figure 15:
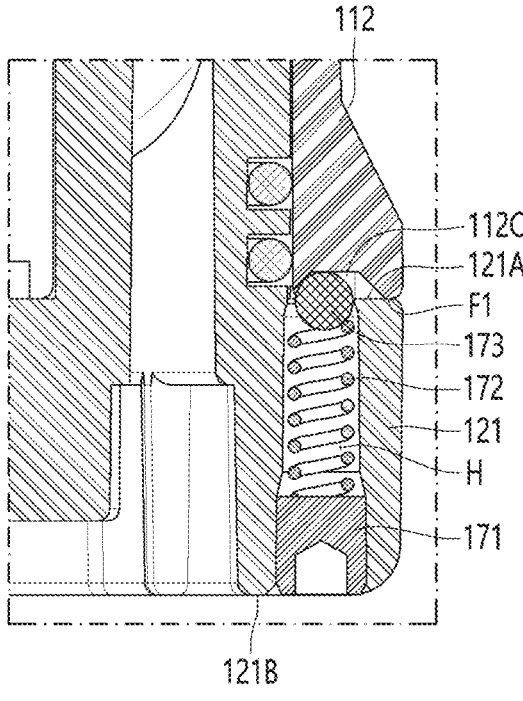
FIG. 15 is a cross-sectional view of the screen changing device taken along line 15-15 of FIG. 3 according to an embodiment.

100: device
10: apparatus
101: first syringe, 101A: first container, 101B: first plunger
102: second syringe, 102A: second container, 102B: second plunger
110: first housing
111: first base, 111A: first base surface, 111B: second base surface
112: outer wall, 112A: first outer surface, 112B: first inner surface, 112C: guide groove
113: inner wall, 113A: second outer surface, 113B: second inner surface
114: first connector, 115: second connector, 116: third connector, 117: fourth connector
114A: first protrusion, 115A: second protrusion, 116A: third protrusion, 117A: fourth protrusion
114B, 116B: thread
118: recess
120: second housing
121: second base, 121A: third base surface, 121B: fourth base surface, 121C: side base surface, 121D: concave portion
122: supporting wall, 122A: base supporting surface, 122B: outer supporting surface, 122C: inner supporting surface
123: recess, 123A: recess bottom surface, 123B: recess side surface, 123C: opening, 123D: lift rim, 123E: recess inclination surface
130A: first screen, 130B: second screen, 130C: third screen, 130D: fourth screen
140: cap, 140A: first cap surface, 140B: second cap surface, 140C: side cap surface 140D: first recess cap surface, 140E: second recess cap surface, 140F: third recess cap surface
141: cap opening
143: second rib
144: tab
145: cap guide surface
146: cap groove
150: cap body
161: first sealing, 162: second sealing, 163: third sealing, 164: fourth sealing, 165: fifth sealing, 166: sixth sealing
171: fixing member
172: elastic member
173: ball
180: channel adapter, 181: first adapter, 182: second adapter, 183: integrated connection body
230, 330: screen
231, 331: plate
232: through-hole
2321, 3321: edge
2322, 3322: protrusion

DETAILED DESCRIPTION OF THE EMBODIMENTS

Hereafter, embodiments are described in detail with reference to the accompanying drawings. However, the embodiments may be modified in various ways, so the right range of the application is not limited to the embodiments.

All of modifications, equivalents, and replacements of the embodiments should be understood as being included in the right range.

The terms used in embodiments are used only for description and should not be construed as being intended to limit the present disclosure. Singular forms are intended to include plural forms unless the context clearly indicates otherwise. It will be further understood that the terms "comprises" or "have" used in this specification, specify the presence of stated features, steps, operations, components, parts, or a combination thereof, but do not preclude the presence or addition of one or more other features, numerals, steps, operations, components, parts, or a combination thereof.

Unless defined otherwise, it is to be understood that all the terms used in the specification including technical and scientific terms has the same meaning as those that are understood by those who skilled in the art. It will be further understood that terms such as terms defined in common dictionaries should be interpreted as having a meaning that is consistent with their meaning in the context of this specification and the relevant art and will not be interpreted in an idealized or overly formal sense unless expressly so defined herein.

Further, in description of the accompanying drawing, same components are given the same reference numerals regardless of the figure numbers and are not repeatedly described. However, in describing embodiments, detailed descriptions of well-known technologies will be omitted so as not to obscure the description of the embodiments with unnecessary detail Further, terms "first", "second", "A", "B", "(a)", and "(b)" can be used in the following description of the components of embodiments. These terms are provided only for discriminating components from other components and, the essence, sequence, or order of the components are not limited by the terms. When a component is described as being "connected", "combined", or "coupled" with another component, it should be understood that the component may be connected or coupled to another component directly or with another component interposing therebetween.

A component included in any one embodiment and a component having the same function are described using the same name in other embodiments. Unless there is contrary statement, description of any one embodiment may be applied to another embodiment and detailed description is omitted within a repeated range.

Referring to FIGS. 1 to 15, a screen changing device 100 may be configured to align any one screen (e.g., a first screen 130A) of a plurality of screens 130A, 130B, 130C, and 130D with a channel P and to align another one screen (e.g., a second screen 130B) with the channel P.

The screen changing device 100 may include a first housing 110. The first housing 110 may be a relatively fixed part.

The first housing 110 may include a first base 111. The first base 111 may include a first base surface 111A (e.g., a top) and a second base surface 111b (e.g., a bottom) opposite to the first base surface 111A.

The first housing 110 may include an outer wall 112. The outer wall 112 may be connected to the outer edge of the first base 111. The outer wall 112 may include a first outer surface 112A (e.g., substantially perpendicularly) crossing each of the first base surface 111A and the second base surface 111B, and a first inner surface 112B being opposite to the first outer surface 112A and (e.g., substantially perpendicularly) crossing each of the first base surface 111A and the second base surface 111B.

The first housing 110 may include an inner wall 113. The inner wall 113 may be connected to the inner edge of the first base 111. The inner wall 113 may include a second outer surface 113A (e.g., substantially perpendicularly) crossing each of the first base surface 111A and the second base surface 111B, and a second inner surface 113B being opposite to the second outer surface 113A and (e.g., substantially perpendicularly) crossing each of the first base surface 111A and the second base surface 111B. The second inner surface 113B may face the first inner surface 112B.

The first inner surface 112B and the second inner surface 113B may be spaced apart from each other. A first space S1 may be defined between the first inner surface 112B of the outer wall 112 and the second inner surface 113B of the inner wall 113. The second outer surface 113A may define a second space S2.

The first housing 110 may include a first connector 114. The first connector 114 may be disposed on the outer wall 112. The first connector 114 may include a first protrusion 114A protruding in one direction (e.g., +Y direction) from the first outer surface 112A of the outer wall 112. The first connector 114 may include a thread 114B formed on at least a portion of the outer surface of the first protrusion 114A. The first connector 114 may include a first passage P1 defined in the first protrusion 114A. The first passage P1 may be connected to the first space S1.

The first housing 110 may include a second connector 115. The second connector 115 may be disposed on the inner wall 113. The second connector 115 may be disposed in the second space S2. The second connector 115 may include a second protrusion 115A protruding from the second outer surface 113A of the inner wall 113. The second protrusion 115A may include a first extension E1 extending in one direction (e.g., −Y direction) from the second outer surface 113A. The second protrusion 115A may include a second extension E2 extending from the first extension E1 in another direction (e.g., +Z direction) (e.g., substantially perpendicularly) crossing the extension direction of the first extension E1. The second connector 115 may include a second passage P2 defined in the second protrusion 115A. The second passage P2 may be connected to the second space S2. The second passage P2 may include a first extension passage P21 defined in the first extension E1. The first extension passage P21 may be connected to the first space S1. The second passage P2 may include a second extension passage P22 defined in the second extension E2. The second extension passage P22 may be connected to the first extension passage P21.

The first passage P1, the first space S1, and the second passage P2 may form one channel P.

The first housing 110 may include a third connector 116. The third connector 116 may be disposed on the outer wall 112. The third connector 116 may be spaced apart from the first connector 114 along the outer wall 112 in the circumferential direction of the first housing 110. The third connector 116 may include a third protrusion 116A protruding in one direction (e.g., +X direction) from the outer wall 112. The third connector 116 may include a thread 116B formed on at least a portion of the outer surface of the third protrusion 116A. The third connector 116 may include a third passage P3 defined in the third protrusion 116A. The third passage P3 may be connected to the first space S1.

The first housing 110 may include a fourth connector 117. The fourth connector 117 may be disposed on the inner wall 113. The fourth connector 117 may be spaced apart from the second connector 115 along the inner wall 113 in the circumferential direction of the first housing 110. The fourth connector 117 may be disposed in the second space S2. The fourth connector 117 may include a fourth protrusion 117A protruding from the second outer surface 113A of the inner wall 113. The fourth protrusion 117A may include a third extension E3 extending in one direction (e.g., –X direction) from the second outer surface 113A. The fourth protrusion 117A may include a fourth extension E4 extending from the third extension E3 in another direction (e.g., +Z direction) (e.g., substantially perpendicularly) crossing the extension direction of the third extension E3. The fourth connector 117 may include a fourth passage P4 defined in the fourth protrusion 117A. The fourth passage P4 may be connected to the second space S2. The fourth passage P4 may include a third extension passage P41 defined in the third extension E3. The third extension passage P41 may be connected to the first space S1. The fourth passage P4 may include a fourth extension passage P42 defined in the fourth extension E4. The fourth extension passage P42 may be connected to the third extension passage P41.

The first housing 110 may include a side recess 118. The side recess 118 may be formed at an end (e.g., a –Z-directional end) that is opposite to the end connected to the first base 111 of the ends of the inner wall 113. The side recess 118 may be formed on the second outer surface 113A toward the second inner surface 113B of the inner wall 113. The side recess 118 may extend in the circumferential direction of the second outer surface 113A.

The first housing 110 may include a flange portion F1. The flange portion F1 may be radially formed from at least a portion of the outer wall 112.

The first housing 110 may include a plurality of guide grooves 112C. The plurality of guide grooves 112C may be formed at the flange portion F1.

The first housing 110 may include a first indicator AR1. The first indicator AR1 can show the rotation direction of a component (e.g., the second housing 120) with respect to the first housing 110 around a rotation axis A-A. For example, the first indicator AR1 may include an arrow shape. The first indicator AR1 may be disposed on the first base surface 111A of the first base 111. The first indicator AR1 may include a plurality of arrow shapes arranged in the circumferential direction of the first housing 110.

The screen changing device 100 may include a second housing 120. The first housing 120 may be a relatively rotating part. For example, the second housing 120 may be configured to rotate about the rotation axis A-A with respect to the first housing 110.

The second housing 120 may include a second base 121. The second base 121 may include a third base surface 121A (e.g., a top), a fourth base 121B (e.g., a bottom) opposite to the third base 121A, and a side base surface 121C between the third base surface 121A and the fourth base surface 121B. The second base 121 may include a concave portion 121D. The concave portion 121D may be formed on at least a portion of the fourth base surface 121B toward the third base surface 121A (e.g., in the +Z direction).

The second base 121 may include a plurality of holes H. The holes H may be formed between the third base surface 121A and the fourth base surface 121B.

The second housing 120 may include a supporting wall 122. The supporting wall 122 may extend in one direction (e.g., +Z direction) from the third base surface 121A of the second base 121. The supporting wall 122 may include an outer supporting surface 122B connected to the outer edge of an base supporting surface 122A and (e.g., substantially perpendicularly) crossing a base supporting surface 122A, and an inner supporting surface 122C connected to the inner edge of the base supporting surface 122A, e.g., substantially perpendicularly) crossing the base supporting surface 122A, and being opposite to the outer supporting surface 122B.

The supporting wall 122 may be disposed in the first space S1. The supporting wall 122 may be surrounded by the base 111, the inner wall 113, and the outer wall 112. An end of the inner wall 113 and an end of the outer wall 112 may be disposed on the third base surface 121A. The base supporting surface 122A may face the second base surface 111B. The base supporting surface 122A may be in contact with the second base surface 111B. The outer supporting surface 122B may face the first inner surface 112B. The outer supporting surface 122B may be in contact with the first inner surface 112B. The inner supporting surface 122C may face the second inner surface 113B. The inner supporting surface 122C may be in contact with the second inner surface 113B.

The inner supporting surface 122C may define a third space S3. The inner wall 113 may be disposed in the third space S3.

The second housing 120 may include a plurality of recesses 123. The plurality of recesses 123 may be arranged in the circumferential direction of the supporting wall 122. For example, four recesses 123 may be spaced about 90 degrees apart from each other around a rotation axis in the circumferential direction of the second housing 120. The plurality of recesses 123 may be formed on the outer supporting surface 122B toward the inner supporting surface 122C.

The plurality of recesses 123 each may include a recess bottom surface 123A. The plurality of recesses 123 each may include a recess side surface 123B connecting the recess bottom surface 123A and the outer supporting surface 122B. The recess side surface 123B may (e.g., substantially perpendicularly) cross the recess bottom surface 123A and/ or the outer supporting surface 122B.

The plurality of recesses 123 each may include an opening 123C. The opening 123C may be disposed on the recess bottom surface 123A. The openings 123C may form a portion of the channel P. For example, the channel P may be defined to continue from the first passage P1 defined in the first connector 114 to the second passage P2 through the opening 123C.

The plurality of recesses 123 may include a lift rim 123D. The lift rim 123D may be disposed on the recess bottom surface 123A. The lift rim 123D may be spaced apart from the recess bottom surface 123B. The lift rim 123D may surround the opening 123C.

The plurality of recesses 123 each may include a recess inclination surface 123E. The recess bottom surface 123A and the recess inclination surface 123E may have a conical shape inclined toward the opening 123C. The recess bottom surface 123A and the recess inclination surface 123E can smoothly guide a living tissue to the opening 123C.

The second housing 120 may include a first groove G1. The first groove G1 may extend in the circumferential direction of the second housing 120. The first groove G1 may be formed on the base supporting surface 122A.

The second housing 120 may include a plurality of second grooves G2. The second groove G2 may be defined between the lift rim 123D and the recess side surface 123B.

The second housing 120 may include a plurality of third grooves G3. The third groove G3 may be formed in one direction (e.g., +Z direction) on the recess side surface 123B.

The third groove G3 may extend along the recess side surface 123B between the outer supporting surface 122B and the recess bottom surface 123A.

The second housing 120 may include a plurality of fourth grooves G4. The plurality of fourth grooves G4 may be disposed in a region closer to the third base surface 121A than the base supporting surface 122A of regions of the outer supporting surface 122B. The plurality of fourth grooves G4 may be disposed between the recess 123 and the second base 121.

The second housing 120 may include a plurality of fifth grooves G5. The fifth grooves G5 may be disposed on the inner supporting surface 122C. The fifth groove G5 may surround the opening 123C. The fifth groove G5 may form a closed loop extending around the opening 123C.

The second housing 120 may include a plurality of first ribs R. The plurality of first ribs R may be configured to support a plurality of screens 130A, 130B, 130C, and 130D in one direction (e.g., radially outward). The plurality of first ribs R may be disposed on the recess bottom surface 123A. The plurality of first ribs R may be arranged around the opening 123C. For example, three first ribs R may be spaced about 120 degrees apart from each other. The plurality of first ribs R may extend toward the recess side surface 123B from the opening 123C.

The second housing 120 may include a plurality of bosses B. The plurality of bosses B may be disposed on the lift rim 123D. The plurality of bosses B may be disposed in the circumferential direction of the lift rim 123D. For example, four bosses B may be spaced about 90 degrees apart from each other. Virtual extension lines connecting the bosses B and the opening 123C may not intersect the first ribs R.

The first housing 120 may include a second indicator AR2. The second indictor AR2 can show the positions of the plurality of screens 130A, 130B, 130C, 130D. For example, the second indictor AR2 can show numbers corresponding to the plurality of screens 130A, 130B, 130C, and 130D, respectively. The second indicator AR2 may be disposed on a surface of the concaved portion 121D (e.g., the bottom surface).

The first housing 120 may include a third indicator AR3. The third indicator AR3 can show the rotation direction of the second housing 120 with respect to the first housing 110 around the rotation axis A-A. For example, the third indicator AR3 may include an arrow shape. The third indicator AR3 may be disposed on a surface of the concaved portion 121D (e.g., the bottom surface). The third indicator AR3 may include a plurality of arrow shapes arranged in the circumferential direction of the second housing 120.

The screen changing device 100 may include a plurality of screens 130A, 130B, 130C, and 130D configured to reduce the size of a living tissue. For example, the screen changing device 100 may include a first screen 130A, a second screen 130B, a third screen 130C, and a fourth screen 140D.

The plurality of screens 130A, 130B, 130C, and 130D each may be disposed on one corresponding recess 123.

Any one screen of the plurality of screens 130A, 130B, 130C, and 130D may be configured to be aligned with the first connector 114 and the second connector 115. For example, the first screen 130A may be aligned with the first connector 114 and the second connector 115. For example, a channel P continuing from the first passage P1 to the second passage P2 through the first screen 130A and an opening 123A may be defined. Meanwhile, when the first screen 130A is aligned with the first connector 114 and the second connector 115, other screens (e.g., the second screen 130B, the third screen 130C, and the fourth screen 140D) may not be aligned with the first connector 114 and the second connector 115.

Any one screen of the plurality of screens 130A, 130B, 130C, and 130D may be configured to be aligned with the third connector 116 and the fourth connector 117. For example, the second screen 130B may be aligned with the third connector 116 and the fourth connector 117. A channel continuing from the third passage P3 defined in the third connector 116 to the fourth passage P4 through the second screen 130B and an opening 123A may be defined. Meanwhile, when the second screen 130B is aligned with the third connector 116 and the fourth connector 117, other screens (e.g., the first screen 130A, the third screen 130C, and the fourth screen 140D) may not be aligned with the third connector 116 and the fourth connector 117.

The screen changing device 100 may include a plurality of caps 140. The plurality of caps 140 may be configured to each retain corresponding one of the plurality of screens 130A, 130B, 130C, and 130D in the recesses 123 in which the screens 130A, 130B, 130C, and 130D are disposed, respectively.

The plurality of caps 140 each may include a first cap surface 140A (e.g., a front surface), a second cap surface 140B (e.g., a rear surface) opposite to the first cap surface 140A, and a side cap surface 140C between the first cap surface 140A and the second cap surface 140B. The second cap surface 140B may face corresponding one of the screens 130A, 130B, 130C, and 130D. The side cap surface 140C may face the recess side surface 123B The plurality of caps 140 each may include a first recess cap surface 140D formed on the second cap surface 140B toward the first cap surface 140A (e.g., +Y direction). The first recess cap surface 140D may be formed inside the second cap surface 140B.

The plurality of caps 140 each may include a second recess cap surface 140E formed on the first recess cap surface 140D toward the first cap surface 140A (e.g., +Y direction). The second recess cap surface 140E may be formed inside the first recess cap surface 140D. The second recess cap surface 140E may include a conical shape inclined toward a cap opening 141. The second recess cap surface 140E can smoothly guide a living tissue to the cap opening 141.

The plurality of caps 140 each may include a third recess cap surface 140F formed on the second cap surface 140B toward the first cap surface 140A (e.g., +Y direction). The third recess cap surface 140F may be formed outside the second cap surface 140B.

The plurality of caps 140 each may include a cap opening 141. The cap opening 141 may be aligned with the opening 123C. The cap opening 141 may be positioned substantially on the same line as the opening 123C. The cap opening 141 may be aligned with the first passage P1 and/or the third passage P3. The cap opening 141 may be positioned substantially on the same line as the first passage P1 and/or the third passage P3.

The plurality of recesses 140 each may include a plurality of holes 142. The plurality of holes 142 may be configured to be each fitted on one corresponding boss B. The plurality of holes 142 may be disposed on the first recess cap surface 140D. The plurality of holes 142 may be arranged in the circumferential direction of the cap 140.

The plurality of caps 140 each may include a plurality of second ribs 143. The plurality of second ribs 143 may be configured to support the plurality of screens 130A, 130B, 130C, and 130D in one direction (e.g., radially inward). The plurality of second ribs 143 may be disposed on the second recess cap surface 140E. The plurality of second ribs 143 may be arranged around the cap opening 141. The plurality of second ribs 143 may extend radially outward from the cap opening 141. The plurality of second ribs 143 may not at least partially overlap the plurality of first ribs R.

The plurality of caps 140 may include a tab 144. The tab 144 may be configured to be fitted in the third groove G3. The tab 144 may extend between the first cap surface 140A and the second cap surface 140B. The tab 144 may be connected to the first cap surface 140A. The tab 144 may be connected to the third recess cap surface 140F.

The plurality of caps 140 each may include a cap guide surface 145. The cap groove 145 may be disposed around the cap opening 141. The cap guide surface 145 may be formed on the second recess cap surface 140E. The cap guide surface 145 may include a conical shape inclined toward a cap opening 141. The cap guide surface 145 can smoothly guide a living tissue to the cap opening 141.

The plurality of caps 140 each may include a cap groove 146. The cap groove 146 may be disposed around the cap opening 141. The cap groove 140A may be disposed on the first cap surface 140A. The cap groove 146 may extend around the cap opening 141.

The screen changing device 100 may include cap body 150. The cap body 150 may include a flange shape. At least a portion of the cap body 150 may be accommodated in the side recess 118. The cap body 150 may be disposed in the second space S2 between the inner walls 113. The lower body 150 may be disposed on the base 121.

The screen changing device 100 may include a plurality of first sealings 161. The first sealing 161 may be configured to seal the gap between the cap 140 and the first passage P1. The first sealing 161 may be configured to seal the gap between the cap body 150 and the third passage P3. The first sealing 161 may be disposed between the cap 140 and the outer wall 112. For example, the first sealing 161 may be disposed in the cap groove 146.

The screen changing device 100 may include a plurality of second sealings 162. The second sealing 162 may be configured to seal the gap between the supporting wall 122 and one corresponding cap 140. The second housing 162 may be disposed in the second groove G2.

The screen changing device 100 may include a plurality of third sealings 163. The third sealing 163 may be configured to seal the gap between the inner wall 113 and the supporting wall 122. The third housing 163 may be disposed in the fourth groove G5.

The screen changing device 100 may include a fourth sealing 164. The fourth sealing 164 may be configured to seal the gap between the cap body 150 and the inner wall 113. The fourth sealing 164 may be disposed on a stepped region of the cap body 150.

The screen changing device 100 may include a fifth sealing 165. The fifth sealing 165 may be configured to seal the gap between the first base 111 and the supporting wall 122. The fifth sealing 165 may be disposed in the first groove G1.

The screen changing device 100 may include a plurality of sixth sealings 166. The sixth sealings 166 may be configured to seal the gap between the outer wall 112 and the supporting wall 122. The plurality of sixth sealings 166 each may be disposed in one corresponding fourth grooves G4.

The screen changing device 100 may include fixing members 171. The fixing members 171 may be disposed in the holes H. A side surface of the fixing member 171 may be in surface contact with a side surface of the hole H. A surface (e.g., a bottom) of the fixing member 171 may be in the same plane as the fourth base surface 121B.

The screen changing device 100 may include elastic members 172. The elastic members 172 may be disposed in the holes H and on the fixing members 171. For example, the elastic member 172 may be compression spring.

The screen changing device 100 may include balls 173. The ball 173 may be at least partially accommodated in the guide groove 112C. The ball 173 may be disposed between the guide groove 112C and the elastic member 172. The elastic members 172, the balls 173, and the guide grooves 112C can determine the position of the second housing 120 with respect to the first housing 110.

The screen changing device 100 may include a channel adapter 180. The channel adapter 180 enables the second connector 115 and/or the fourth connector 117 to be coupled to another container. For example, the channel adapter 180 may include a first adaptor 181 configured to be connected to the second connector 115 and a second adapter 182 configured to be connected to the fourth connector 117. The first adapter 181 and the second adapter 182 may form a portion of the channel P. The channel adapter 180 may include a connection body 183 formed by integrating the first adapter 181 and the second adapter 182.

FIG. is a view of a screen changing device having a first configuration according to an embodiment.

Figure 16:
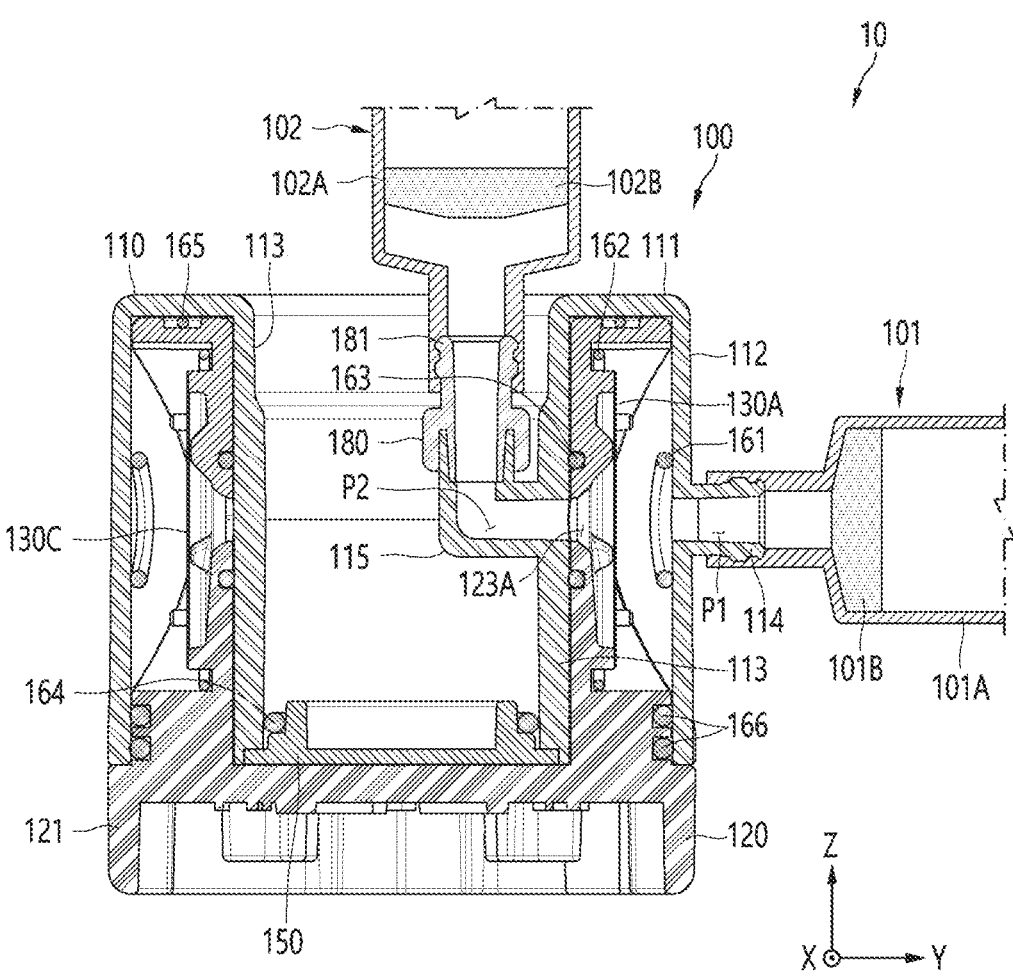
FIG. 16 is a view of a screen changing device having a first configuration according to an embodiment.

Referring to FIG. 16, an apparatus 10 may be configured to reduce the size of a living tissue. For example, the living tissue may include a fat tissue from a person or an animal. The apparatus 10 may include a first syringe 101, a second syringe 102, and the screen changing device 100. The first syringe 101 may include a first container 101A configured to keep a living tissue, and a first plunger 101B configured to pressurize the internal space of the first container 101A. The first container 101A may be coupled to the first connector 114. The second syringe 102 may include a second container 102A configured to keep a living tissue, and a second plunger 102B configured to pressurize the internal space of the second container 102A. The second container 102A may be coupled to the second connector 115 and/or the first adapter 181. A portion of the first plunger 101B and a portion of the second plunger 102B are omitted in FIG. 16, but those skilled in the art would understand that the first plunger 101B may have various shapes.

A method of using the apparatus 10 according to an embodiment may include a step of providing a living tissue into the first container 101A and/or the second container 101B. Thereafter, the method may include a step of coupling the first syringe 101 and the second syringe 102. The method may include a step of aligning the first connector 114, the second connector 115, and one screen of a plurality of screens (e.g., the first screen 130A). The method may include a step of pressurizing the internal space of the first container 101A and the internal space of the second container 101B with the first plunger 101A and the second plunger 101B, respectively. The internal space of the first container 101A and the internal space of the second container 101B may be alternately pressurized. When the internal space of the first container 101A is pressurized, the living tissue in the first container 101A can pass through the first screen 130A along the first passage P1 and can move into the internal space of the second container 102A along the second passage P2. When the internal space of the second container 102A is pressurized, the living tissue in the second container 102A can pass through the first screen 130A along the second passage P2 and can move into the internal space of the first container 101A along the first passage P1. The steps described above may be repeated. The size of a living tissue can be reduced while the steps are repeated.

Figure 17:
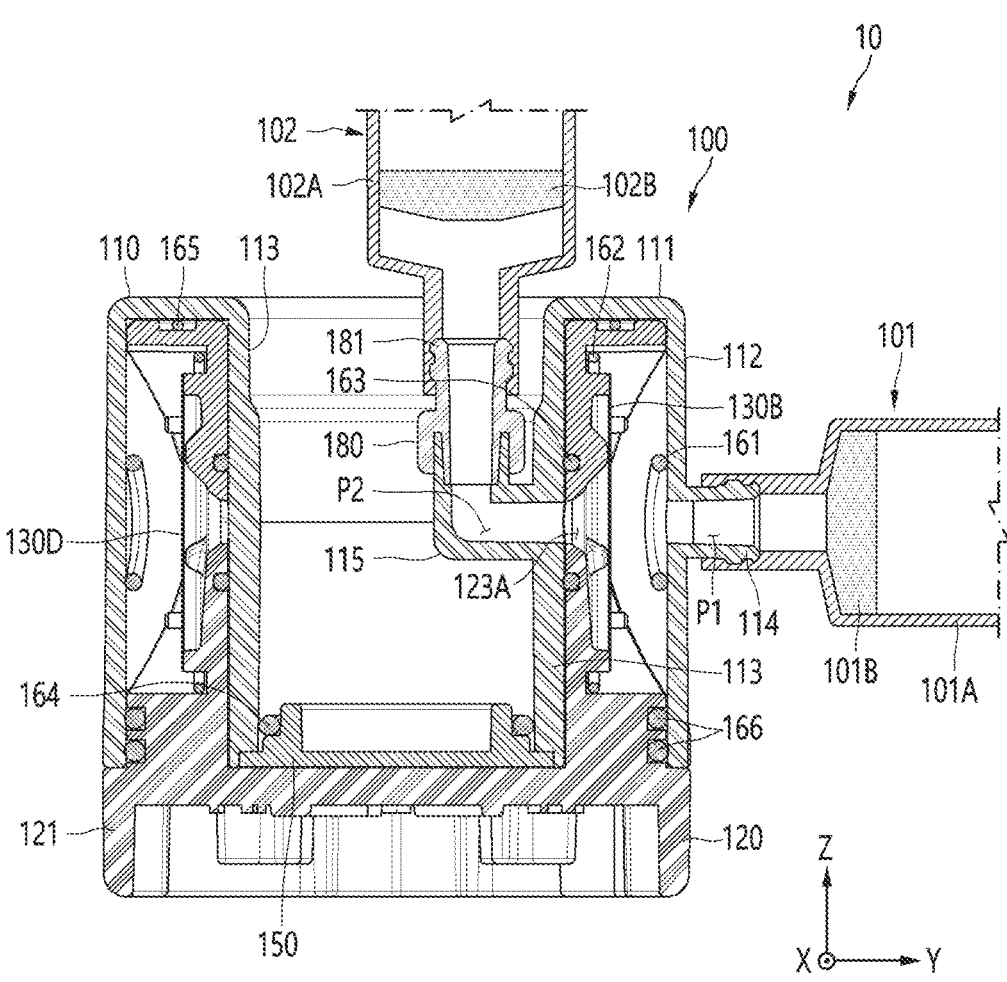
FIG. 17 is a view of a screen changing device having a second configuration according to an embodiment.

FIG. 17 is a view of a screen changing device having a second configuration according to an embodiment.

Referring to FIG. 17, the method of using the apparatus 10 may include a step of shifting the first screen 130A aligned with the first connector 114 and the second connector 115 in FIG. 16. The moving operation may be achieved by rotating the second housing 120 about the rotation axis A-A. Thereafter, the method may include a step of aligning the second screen 130B with the first connector 114 and the second connector 115 by rotating the second housing 120 about the rotation axis A-A. Thereafter, the pressurizing operation described with reference to FIG. 16 may be performed at least once.

A user can selectively change the plurality of screens 130A, 130B, 130C, and 130D aligned between the first connector 114 and the second connector 115 without separating the first syringe 101 and the second syringe 102 from the apparatus through the aligning step and the shifting step.

In an embodiment, a user can couple the first syringe 101 and the second syringe 102 to the third connector 116 and the fourth connector 117 between the aligning step and the shifting step.

Figure 18:
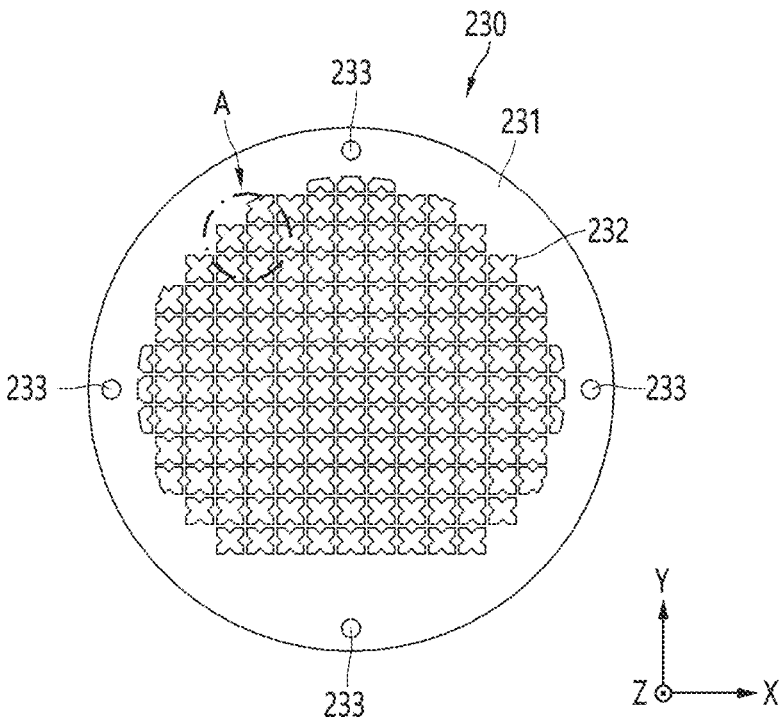
FIG. 18 is a plan view of a screen according to an embodiment.
Figure 19:
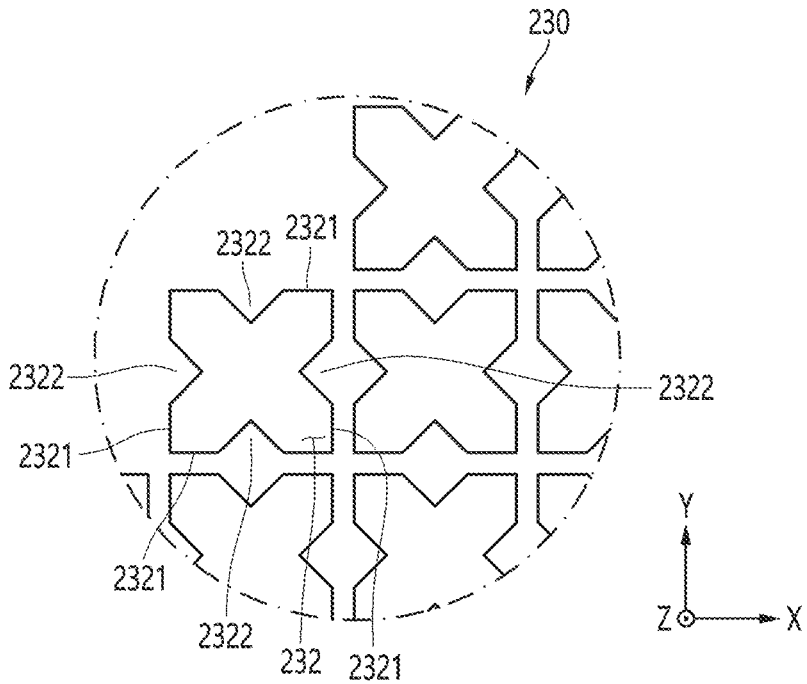
FIG. 19 is an enlarged view of the part A of the screen of FIG. 18 according to an embodiment.

FIG. 18 is a plan view of a screen according to an embodiment. FIG. 19 is an enlarged view of the part A of the screen of FIG. 18 according to an embodiment.

Referring to FIGS. 18 and 19, a screen 230 (e.g., the first screen 130A, the second screen 130B, the third screen 130C, and/or the fourth screen 130D) may include a plate 231. The plate 231 may have a disc shape substantially having a circular or elliptical cross-section. The plate 231 may include a metal material.

The screen 230 may include a plurality of through-holes 232 formed through the front and rear of the plate 231. A living tissue can be pressurized by the first plunger 101B and the second plunger 102B in the internal space of a first container (e.g., the first container 101A in FIGS. 16 and 17) of a first syringe and the internal space of a second container (e.g., the second container 101B in FIGS. 16 and 17) of a second syringe.

Pressurizing the first container and the second container may be performed by other tools rather than limited to the first plunger 101B and the second plunger 102B. A pressurized (e.g., air pressure) living tissue can flow into the internal space of a first container (e.g., the first container 101A in FIGS. 16 and 17) of a first syringe and the internal space of a second container (e.g., the second container 101B in FIGS. 16 and 17) of a second syringe through the plurality of through-holes 232 of the screen 230. While the living tissue pressurized in the internal space of the first container and the internal space of the second container flows through the plurality of through-holes 232, the living tissue may be pressurized by at least one edge 2321 defining the through-holes 232 having an area smaller than the cross-section of the channel P. The living tissue may be scratched and torn by at least one edge 2321.

The living tissue may be sequentially and repeatedly moved into the internal space of a first container of a first syringe and the internal space of a second container of a second syringe by operation of the first plunger 101B and the second plunger 102B. The first plunger 101B and the second plunger 102B may be manually or electrically operated, but the present disclosure is not limited thereto.

The plurality of through-holes 232 may include various shapes. The shape may include the size and/or the form of the through-holes 232. For example, plurality of through-holes 232 may include a circular or elliptical shape substantially defined by one edge 2321 or may include at least one or a combination of polygonal shapes (e.g., a rectangle or a square) defined by a plurality of edges 2321.

The plurality of through-holes 232 each may include a plurality of edges 2321 and a plurality of protrusions 2322. The plurality of protrusions 2322 each may protrude from one corresponding edge 2321 toward an opposite edge 2321. While the living tissue pressurized by the first plunger 101B and the second plunger 102B in the internal space of a first container and the internal space of a second container of a second syringe flows through the plurality of through-holes 232 of the screen 230, the living tissue may be pressurized by at least one edge 2321 defining the through-holes 232 having an area smaller than the cross-section of the channel P, and the protrusions 2322. The plurality of edges 2321 and protrusions 2322 may scratch and tear the living tissue.

The screen 230 may include a plurality of holes 233. The plurality of holes 233 may be configured to be each fitted on one corresponding boss B shown in FIG. 12.

Figure 20:
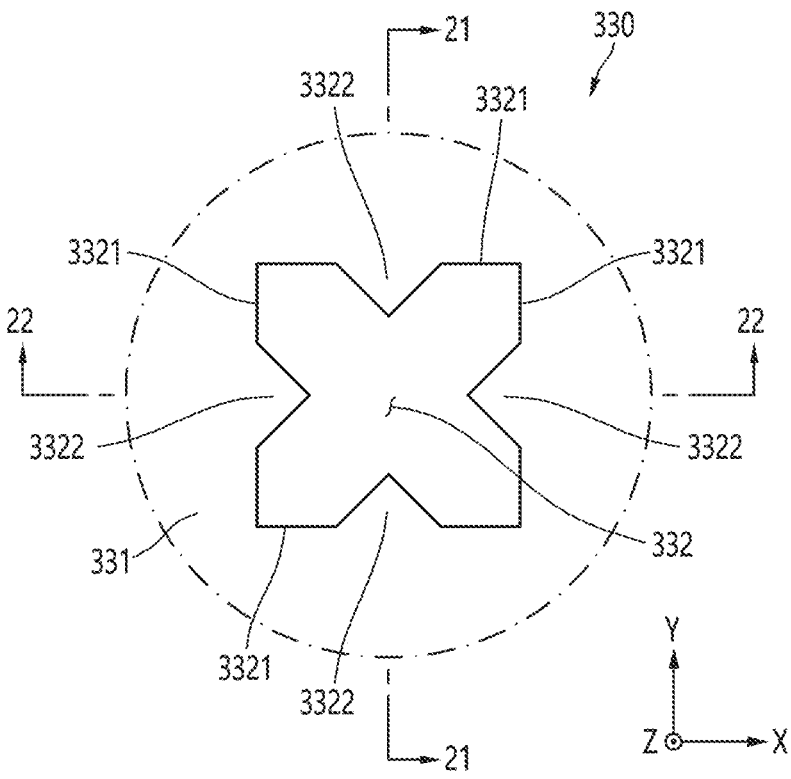
FIG. 20 is an enlarged view of the part A of the screen of FIG. 18 according to an embodiment.
Figure 21:
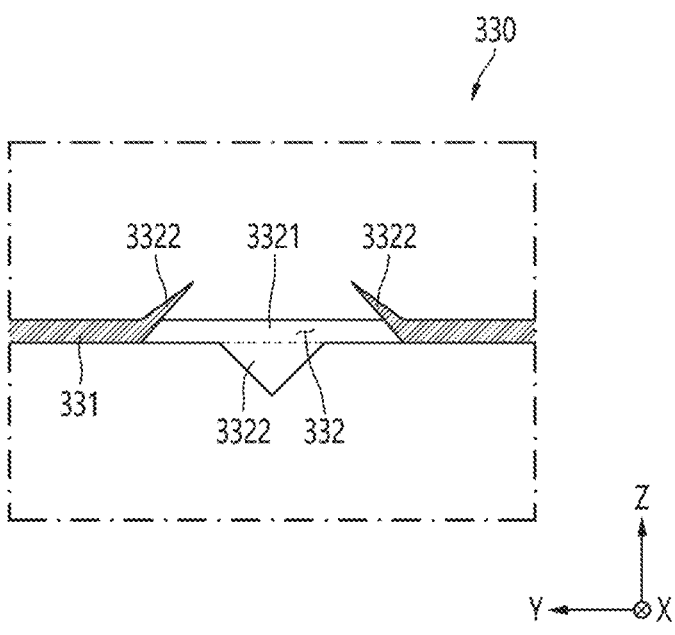
FIG. 21 is a cross-sectional view of the screen taken along line 21-21 of FIG. 20 according to an embodiment.
Figure 22:
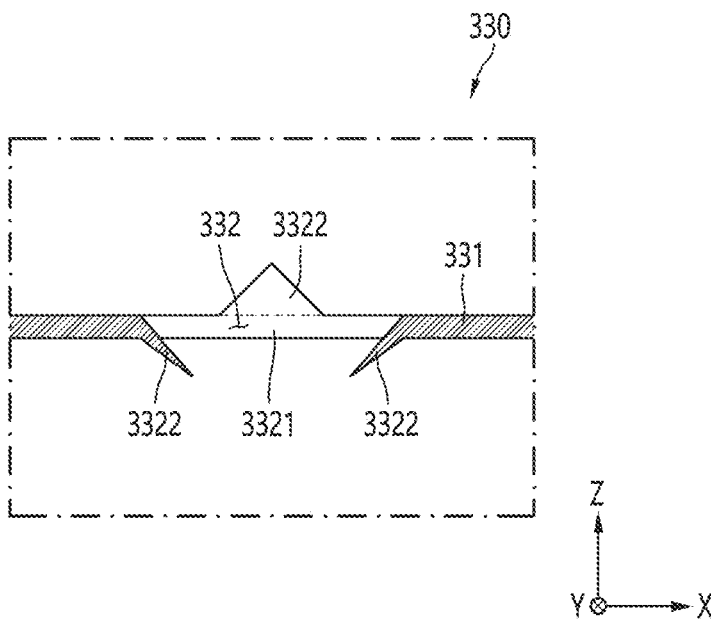
FIG. 22 is a cross-sectional view of the screen taken along line 22-22 of FIG. 20 according to an embodiment.

FIG. 20 is an enlarged view of the part A of the screen of FIG. 18 according to an embodiment. FIG. 21 is a cross-sectional view of the screen of FIG. 20 according to an embodiment taken along line 21-21. FIG. 22 is a cross-sectional view of the screen of FIG. 20 according to an embodiment taken along line 22-22.

Referring to FIGS. 20 and 22, a screen 330 (e.g., the first screen 130A, the second screen 130B, the third screen 130C, and/or the fourth screen 130D, and/or the screen 230) may include a plate 331 and a plurality of through-holes 332. The plurality of through-holes 332 each may be defined by a plurality of edges 3321. The plurality of through-holes 332 each may include a plurality of edges 3321 and a plurality of protrusions 3322.

At least one protrusion 3322 of the plurality of protrusions 3322 may protrude in a first diagonal direction (a direction between the Z axis and the Y axis) at an angle that is not 0 with respect to the plate 331. At least one protrusion 3322 of the plurality of protrusions 3322 may protrude in a second diagonal direction (a direction between the Z axis and the Y axis) that is different from the first diagonal direction at an angle that is not 0 with respect to the plate 331. A virtual extension line in the first diagonal direction may be in a skew position with a virtual extension line in the second diagonal direction.

Figure 23:
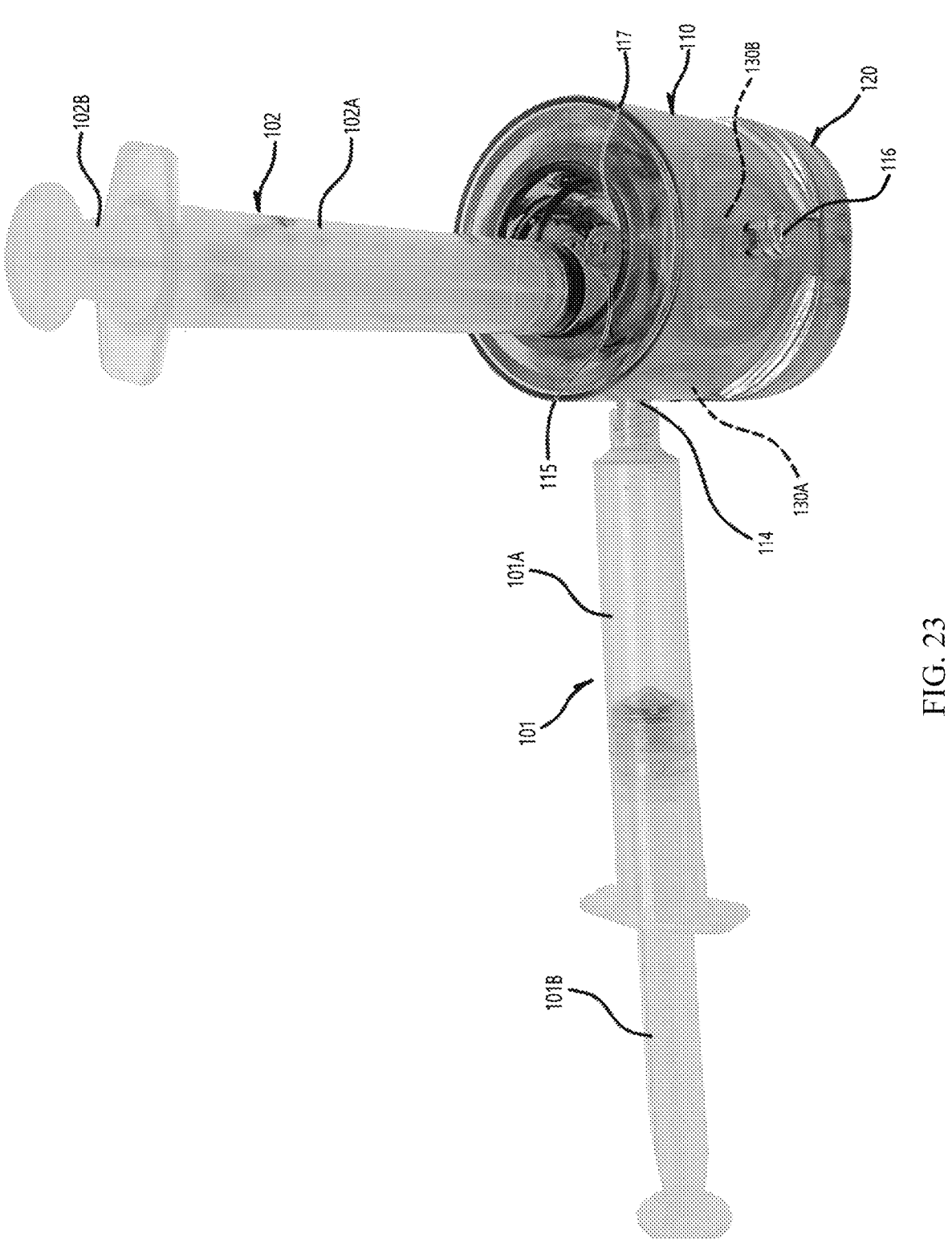
FIG. 23 is a picture of a system for reducing the size of a living tissue using a screen changing device according to an embodiment.

FIG. 23 is a picture of a system for reducing the size of a living tissue using a screen changing device according to an embodiment.

Referring to FIG. 23, four screens are positioned with gaps of 90 degrees, and the first connector 114 and the second connector 115 makes a pair, thereby forming a set of connectors.

A first syringe 101 is fastened to the first connector and a second syringe 115 is fastened to the second connector 115. A living tissue is accommodated in the first syringe 101 and the second syringe 115 is empty.

In this state, when the first syringe 101 is pressurized, the living tissue accommodated in the first syringe 101 passes through the first screen 130A through the first connector 114 and is then accommodated in the second syringe 102 through the second connector 115. Next, the second syringe 102 is pressurized, whereby the living tissue is accommodated back into the first syringe through the first screen 130A. The size of the living tissue is reduced by alternately perform these processes several times.

When the process of reducing the size of a living tissue through the first screen 130A is finished, a process of reducing the size of the living tissue through the second screen 130B having a smaller through-hole size than the first screen is performed. The first connector 114 and the second connector 115 are aligned with the second screen 130B at a right position by rotating the first housing 110 with respect to the second housing 120. Thereafter, the process of reducing the size of the living tissue using the second screen is performed in the same way as the process that uses the first screen 130A. The sizes of the through-holes of four screens are sequentially decreased. Accordingly, the size of a living tissue is gradually reduced by sequentially selecting four screens in which the sizes of the through-holes are sequentially decreased.

The third connector 116 and the fourth connector 117 remain as spares without being connected to a syringe. When a connector cannot be used because a channel through which a living tissue passes is clogged or damaged, syringes are fastened using the third connector and the fourth connector instead of the first connector and the second connector.

Although embodiments were described with reference to the limited drawings, various technical changes and modifications may be possible by those skilled in the art on the basis of the above description. For example, the described technologies may be performed in order different from the described method, and/or even if components such as the described system, structure, device, and circuit are combined or associated in different ways from the description or replaced by other components or equivalents, appropriate results can be accomplished.

Therefore, other implements, other embodiments, and equivalents to the claims are included in the following claims.

What is claimed is:

1. A screen changing device comprising:
a first housing comprising
a first base,
an outer wall connected to the first base,
an inner wall connected to the first base and being opposite to the outer wall,
a first space defined between the outer wall and the inner wall,
a second space defined by the inner wall,
a first connector disposed on the outer wall, and
a second connector disposed on the inner wall and in the second space;
a second housing comprising
a second base,
a supporting wall connected to the second base and disposed in the first space, and
a plurality of recesses arranged in a circumferential direction of the supporting wall; and
a plurality of screens disposed in the plurality of recesses, respectively, and configured to reduce a size of a living tissue,
a body cap disposed between the inner wall and the second base,
wherein the second housing is configured to be rotated with respect to the first housing from a first configuration, in the first configuration, a first screen of the plurality of screens is aligned with the first connector and the second connector to a second configuration, in the second configuration, the first screen is not aligned with the first connector and the second connector and a second screen of the plurality of screens is aligned with the first connector and the second connector.

2. The screen changing device of claim 1, further comprising a plurality of caps configured to retain the first screen, wherein the first screen corresponds to a first recess of the plurality of recesses, and the first screen of the plurality of screens is in the first recess.

3. The screen changing device of claim 2, further comprising a first sealing disposed between the plurality of caps and the outer wall.

4. The screen changing device of claim 2, further comprising a second sealing disposed between the supporting wall and the plurality of caps.

5. The screen changing device of claim 1, further comprising a third sealing disposed between the supporting wall and the inner wall.

6. The screen changing device of claim 1, wherein the first connector comprises:
a first protrusion protruding from the outer wall away from a rotation axis; and
a first passage defined in the first protrusion.

7. The screen changing device of claim 1, wherein the second connector comprises:
a second protrusion protruding from the inner wall; and
a second passage defined in the second protrusion,
wherein the second protrusion comprises:
a first extension extending from the inner wall toward a rotation axis; and
a second extension extending from the first extension in an axial direction of the rotation axis.

8. The screen changing device of claim 1, further comprising:
a guide groove disposed in the first housing;
a ball disposed in the second housing; and
an elastic member disposed between the guide groove and the ball,
wherein the ball and the elastic member are configured to determine a position of the second housing with respect to the first housing.

9. The screen changing device of claim 1, wherein the first housing further comprises:
a third connector disposed on the outer wall; and
a fourth connector disposed on the inner wall and in the second space.

10. The screen changing device of claim 1, further comprising a channel adapter configured to be coupled to the second connector.

11. The screen changing device of claim 1, further comprising
an indicator showing a rotation direction of the second housing.

12. The screen changing device of claim 1, wherein the first screen comprises a first through-hole having a first shape, and the second screen comprises a second through-hole having a second shape different from the first shape.

13. The screen changing device of claim 1, wherein each of the plurality of screens comprises:
a plate; and
a through-hole formed through a front and a rear of the plate and defined by a plurality of edges of the plate,
the plurality of edges each comprises a protrusion protruding toward a center portion of the through-hole, and
while the living tissue pressurized in an internal space of a first syringe and an internal space of a second syringe flows through the through-hole of the each of the plurality of screens disposed in a channel, the plurality of edges and the protrusion of each of the plurality of edges pressurize the living tissue passing through the through-hole and the plurality of edges and the protru-
sion of each of the plurality of edges scratch and tear
the living tissue.

14. The screen changing device of claim 13, wherein:

in the first configuration, when a first plunger of the first
syringe pressurizes an internal space of a first container,
the living tissue in the first syringe is moved into the
second syringe sequentially through a first passage, the
aligned screen, and a second passage; and in the second configuration, when a second plunger of the
second syringe pressurizes an internal space of a sec-
ond container, the living tissue in the second syringe is
moved into the first syringe sequentially through the
second passage, the aligned screen, and the first pas-
sage.

\* \* \* \* \*